(12) United States Patent
Brun-Buisson et al.

(10) Patent No.: US 6,974,883 B2
(45) Date of Patent: Dec. 13, 2005

(54) PROCESS FOR MANUFACTURING TRIETHANOLAMINE AND PRODUCT OBTAINED

(75) Inventors: Daniel Brun-Buisson, Istres (FR); Philippe Villegier, Saint-Mitre les Remparts (FR)

(73) Assignee: BP Chemicals Limited, London (GB)

(*) Notice: Subject to any disclaimer, the term of this patent is extended or adjusted under 35 U.S.C. 154(b) by 0 days.

(21) Appl. No.: 10/734,107

(22) Filed: Dec. 15, 2003

(65) Prior Publication Data

US 2004/0127748 A1 Jul. 1, 2004

Related U.S. Application Data

(62) Division of application No. 10/169,579, filed as application No. PCT/GB01/00216 on Jan. 19, 2001, now Pat. No. 6,683,217.

(30) Foreign Application Priority Data

Jan. 24, 2000 (FR) .................................... 00 00851

(51) Int. Cl.$^7$ ............................................ C07C 215/10
(52) U.S. Cl. .............. 564/506; 252/182.12; 252/182.29
(58) Field of Search ........................................ 564/506

(56) References Cited

U.S. PATENT DOCUMENTS

| 3,849,262 A | 11/1974 | Cocuzza ..................... 203/38 |
| 4,673,762 A | 6/1987 | Paslean et al. |
| 5,292,958 A | 3/1994 | Claud et al. |
| 5,424,482 A | 6/1995 | Overgaard et al. ............. 564/2 |
| 5,545,757 A | 8/1996 | Hammer et al. |
| 5,693,866 A | 12/1997 | Roling et al. |
| 6,388,137 B1 | 5/2002 | Ruider et al. |

FOREIGN PATENT DOCUMENTS

| CA | A-2 961 718 | 11/1992 |
| EP | 0 004 015 A1 | 9/1979 |
| EP | A-673 920 A2 | 9/1995 |
| GB | A-760 215 | 10/1956 |
| JP | A2-62 005939 | 1/1987 |
| WO | WO-A-00/32553 | 6/2000 |

OTHER PUBLICATIONS

Mitsui Toatsu Chem Inc., "High Pure Tri Ethanolamine Preparation Heat Treat Crude Product Absence Oxygen Useful Cosmetic", Derwent Abstract of Japanese Appln. 62005939 , (Jan. 12, 1987).
J.F. Martin, "Colour Contaminate Inhibit Ethanolamine Compound Amine Prevent Formation Oxygen Contain Compound", Derwent Abstract of Canadian Appln. 2061718, (Nov. 23, 1992).
The Merck Index, 12$^{th}$ edition, 1996, Merck & Co., Inc., Whitehouse Station, NJ, p. 1647–1648 entry No. 9798.
Thomas I. McMillan, SRI International Report No. 193 of Jan. 1991, "Ethylene oxide derivatives, " pages 6–11 to 6–17, 6–25 to 6–27, Fig. 6.3 "ethanolamines".
Harold W. Scheeline, SRI Imternational Report No. 70 of Aug. 1971, "Ethylene Glycols, Glycols Ethers and Ethanolamines, " pages 145–147, (Fig. 10, 1, ethanolamines ), 149–153.
Ullmann's Encyclopedia of Industrial Chemistry, 5$^{th}$ ed., 1988, vol. B3, Unit operations II, Chapter 4: Distillation and rectification, in particular pages 4–46 to 4–49.

*Primary Examiner*—Brian Davis
(74) *Attorney, Agent, or Firm*—Finnegan, Henderson, Farabow, Garrett and Dunner, L.L.P.

(57) ABSTRACT

The present invention relates to a continuous process for the manufacture of triethanolamine (TEA) comprising, in succession: (i) a step of synthesizing the TEA by continuously bringing ammonia into contact with ethylene oxide under conditions allowing the formation of a reaction mixture comprising mono-, di- and triethanolamines, (ii) a step of continuously separating the ammonia that has not reacted from the reaction mixture and (iii) a step of continuously separating the TEA from the mixture resulting from step (ii). The process is characterized in that a specific mixture of alkanolamines, comprising TEA and from 0.5 to 50% by weight of at least one secondary dialkanolamine, is prepared or isolated from the mixture resulting from step (ii), and in that the TEA is separated and isolated with a degree of purity equal to or greater than 99.2% by weight, by a continuous distillation of the specific mixture of alkanolamines. The present invention also relates to a colorless TEA having a high purity, that can be obtained by the process according to the invention and especially has a high resistance to coloration.

5 Claims, 2 Drawing Sheets

PROCESS FOR MANUFACTURING TRIETHANOLAMINE AND PRODUCT OBTAINED

RELATED APPLICATIONS

This application is a divisional of application Ser. No. 10/169,579, filed Oct. 18, 2002 now U.S. Pat. No. 6,683,217, which is a §371 of PCT/GB01/00216, filed Jan. 19, 2001, the contents of both of which are incorporated herein by reference.

BACKGROUND OF THE INVENTION

The present invention relates to a process for the continuous manufacture of a colourless triethanolamine, which is stable over time and has a high degree of purity, and to the triethanolamine itself which can be obtained by the process of the present invention.

Triethanolamine (TEA) is widely used in industry, especially in fields such as pharmacy and cosmetology, where it has to satisfy a number of increasingly strict requirements.

Among these requirements, the TEA must be colourless. To this criterion is added the stability, particularly thermal stability, of TEA over time. This is because it has been observed that TEA gradually colours over time, without it being possible to identify the products responsible for the coloration, or being possible to explain the mechanisms which result in the coloration. This phenomenon is furthermore frequently mentioned in specialized encyclopaedias and dictionaries such as "Dictionnaire de la Chimie et de ses Applications" [in English "Dictionary of Chemistry and its Applications"] by C. and R. DUVAL, 3rd edition, Technique et Documentation (Paris) (1978), page 1027.

The TEA must also satisfy purity and toxicity requirements. A high degree of purity is often required. Reducing any traces of toxic by-products is also a determining criterion. Among toxic products, certain secondary amines may especially be distinguished, for example diethanolamine (DEA) which, when in contact with nitrated products, forms nitrosamines, which are known as being toxic and carcinogenic.

Surprisingly, it has been observed that the coloration and instability phenomena in TEA over time occur more often when the TEA is pure, and more particularly for a high purity TEA, for example a TEA of purity equal to or greater than 99%, often called in the trade "TEA 99". These phenomena are accentuated by the fact that to keep the TEA in the liquid state it has to be permanently heated above the ambient temperature, e.g. at a temperature comprised between 50 and 70° C.

Several solutions have already been proposed hitherto, but none of them seems to be advantageous in terms of cost, ease of processing, purity level, degree of toxicology and, above all, stability, particularly thermal stability, over time.

Most of the proposed solutions generally consist in adding a coloration-inhibiting product to the TEA before, during or after the product has been manufactured. Thus, French Patent Application FR 2 138 902 describes the use of a borate of an alkali or alkaline-earth metal, or of a boric acid alkanolamine ester as coloration inhibitor. The resulting TEA has a relatively high sulphuric ash content.

European Patent Application EP 0 004 015 describes the addition of an active amount of phosphorous or hypophosphorous acid or of their derivatives to the TEA, during or after the preparation of the TEA. No colour index of the TEA was measured after the TEA has undergone a hot-ageing test, and no information was given about residual content of secondary dialkanolamine in the TEA.

Canadian Patent Application CA 2,061,718 describes the addition of relatively great amounts of an amine compound such as diethylenetriamine, triethylenetetramine or tetraethylenepentamine to the TEA. However such an addition neither stops, nor limits the coloration of the TEA from yellow to brown colours, after a hot-ageing test.

U.S. Pat. No. 4,673,762 describes the addition of an alkylene oxide such as ethylene oxide or propylene oxide to the TEA. However these compounds are considered as being very toxic and carcinogenic. No information relating to the residual content of secondary dialkanolamine such as DEA in the TEA was given. In addition, the coloration test of the TEA was carried out at a relatively low temperature e.g. at room temperature or at 49° C. (i.e. 120° F.).

U.S. Pat. No. 5,292,958 describes a process for eliminating the diethanolamine (DEA) present in triethanolamine (TEA). The process comprises the addition of glyoxal to the TEA containing DEA, in a molar ratio of glyoxal to DEA greater or equal to 1. However this process does not face the coloration and instability phenomena in TEA over time.

U.S. Pat. No. 5,693,866 describes a process for inhibiting colour formation in crude alkanolamines such as crude TEA. The coloration inhibitors are selected from the group consisting of alkali metal hydroxides or sulfites. However the effect of the inhibition of the coloration only relates to crude TEA.

Although these solutions do solve certain aspects of the coloration problems, e.g. only at relatively low temperature or for crude TEA, they create further problems associated with the presence of these inhibitors, which are often used in great amounts or which are undesirable in the end product because of their toxic nature.

Japanese Patent Application JP 62 005 939 describes a heat-treatment of crude TEA in the absence of oxygen, before distillation of the TEA. However the purified TEA obtained after the distillation of the crude TEA thus treated is still sparingly coloured, before any hot-ageing test of the purified TEA.

Another solution proposed in U.S. Pat. No. 4,567,303 consists in preparing the TEA in a reactor in which the corrosion-sensitive part consists of a stainless steel alloy containing no nickel. This solution does not solve all the problems associated with the coloration and above all the instability of TEA over time.

U.S. Pat. No. 3,819,710 describes a process which consists in carrying out a hydrogenation of the ethanolamines in the presence of hydrogen and of a catalyst. The solution proposed is satisfactory neither from an economic or processibility standpoint, nor from a purity or long-term colour standpoint.

Thus, in the field of the manufacture of ethanolamines there is a need to improve the purity of TEA, especially when the latter is manufactured continuously, directly by bringing ammonia into contact with ethylene oxide. In particular, it has become urgent to reduce the toxic nature of TEA, especially by reducing impurities such as secondary amines, for example DEA formed during the preparation of the TEA. For a number of years now there has also been a need to prevent the coloration of TEA during or after its manufacture, and in particular a need to find a process for the continuous manufacture of TEA which makes the latter colourless and stable, especially thermally stable, over time, without involving, in particular, a coloration-inhibiting agent. There is also a need to find a process for improving the stability, especially thermal stability, of TEA over time and for avoiding any coloration, while at the same time improving its purity level and its non-toxic nature.

A simple method has been found which allows the abovementioned problems to be solved by means of a continuous process for the manufacture, and especially for the purification, of TEA.

SUMMARY OF THE INVENTION

The present invention relates first of all to a continuous process for the manufacture of triethanolamine (TEA) comprising, in succession:
(i) a step of synthesizing the TEA by continuously bringing ammonia into contact with ethylene oxide, especially in an aqueous medium, under conditions allowing the formation of a reaction mixture comprising mono- di- and triethanolamines,
(ii) a step of continuously separating the ammonia that has not reacted from the reaction mixture, the ammonia thus separated being preferably recycled in the synthesis step; and
(iii) a step of continuously separating the TEA from the mixture resulting from step (ii), which process is characterized in that, in the last step, a specific mixture of alkanolamines comprising TEA and from 0.5 to 50% by weight of a secondary dialkanolamine is prepared or isolated from the mixture resulting from step (ii), and in that the TEA is separated and isolated with a degree of purity equal to or greater than 99.2%, preferably equal to or greater than 99.5%, and in particular equal to or greater than 99.7% by weight, by continuous distillation of the specific mixture of alkanolamines.

The term "secondary dialkanolamine" is understood to mean in general a secondary amine or a dialkanolamine which can have the following formula:

in which $R_1$ and $R_2$, which are identical or different, represent alkyl radicals each having a primary, secondary or tertiary alcohol functional group and satisfying, for example, the formula —$C_nH_{2n}OH$ in which n is an integer ranging from 1 to 12, preferably from 2 to 6 or particularly from 2 to 4.

The secondary dialkanolamines that are preferred are chosen from:
diethanolamine (DEA): $HN(CH_2CH_2OH)_2$
diisopropanolamine: $HN(CH_2CHOHCH_3)_2$
di-n-propanolamine: $HN(CH_2CH_2CH_2OH)_2$ and
di-n-butanolamine: $HN(CH_2CH_2CH_2CH_2OH)_2$
Diethanolamine (DEA) is most particularly preferred since it is one of the ethanolamines manufactured at the same time as the TEA during the contact between ammonia and ethylene oxide.

Step (iii) of continuously separating the TEA may comprise a prior step eliminating from the mixture resulting from step (ii) the primary ethanolamine formed during the synthesis step (i), in particular monoethanolamine (MEA) and some of the diethanolamine (DEA) by means of a prior distillation, or preferably at least two prior distillations. This or these prior distillations may be carried out in succession and continuously. It (they) may especially be carried out so as to provide the specific mixture with alkanolamines having, according to the present invention, a particular proportion of DEA, that is to say of secondary dialkanolamine, which mixture will be subjected to the continuous distillation making it possible to separate and isolate the desired TEA, that is to say having a high purity and in the form of a colourless product stable over time.

It is also possible, according to another variant, to add to the mixture resulting from this or these prior distillations a secondary dialkanolamine, for example DEA, if the proportion of the latter is too low in the specific mixture of alkanolamines subjected to the continuous distillation in order to separate and isolate the desired TEA. In this case, the amount of secondary dialkanolamine, for example DEA, added is such that, in total, the proportion of secondary dialkanolamine corresponds to that required according to the present invention in the specific mixture of alkanolamines.

BRIEF DESCRIPTION OF THE INVENTION

Figure 1:
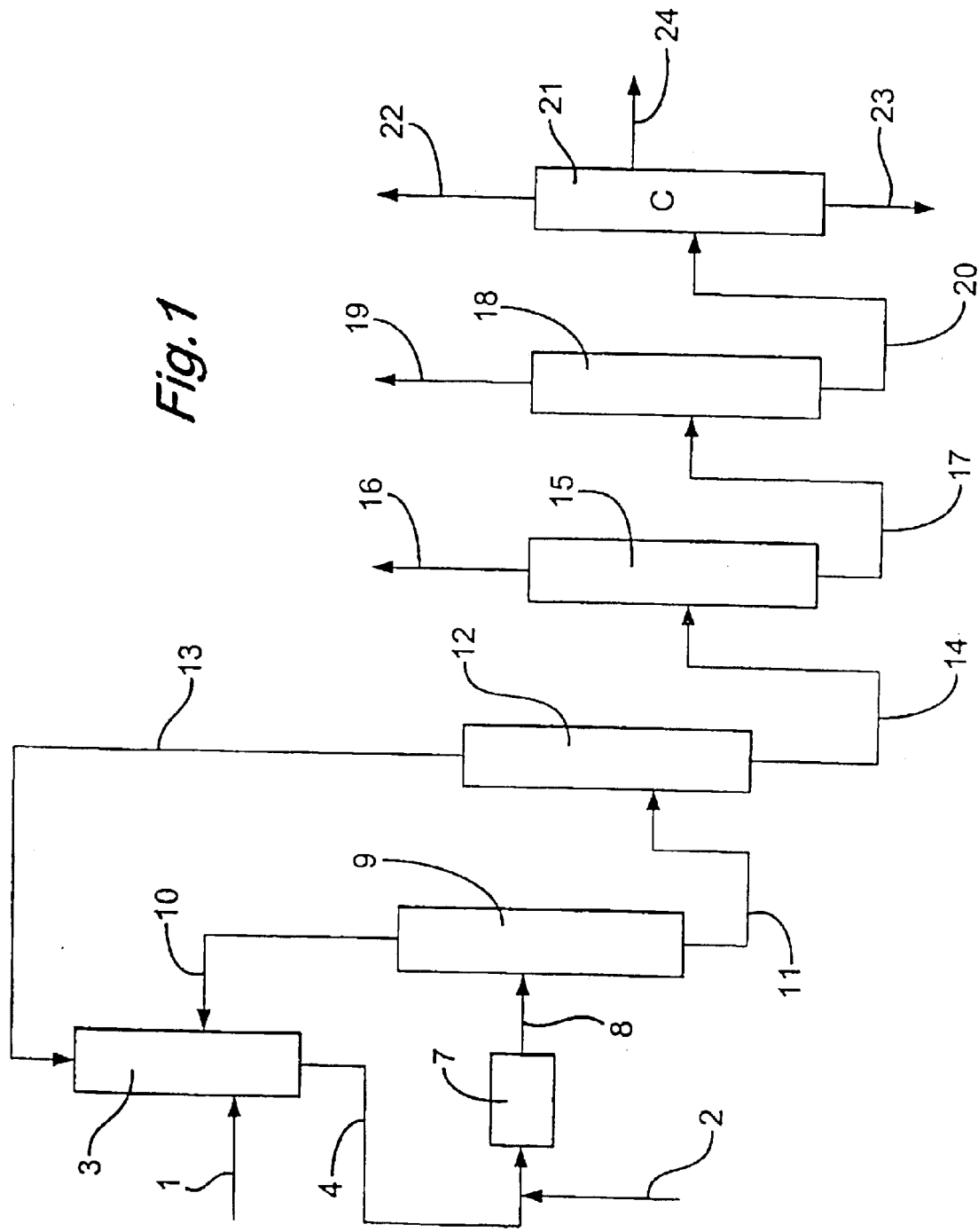
FIG. 1 shows schematically an illustration of the process according to the present invention.
Figure 2:
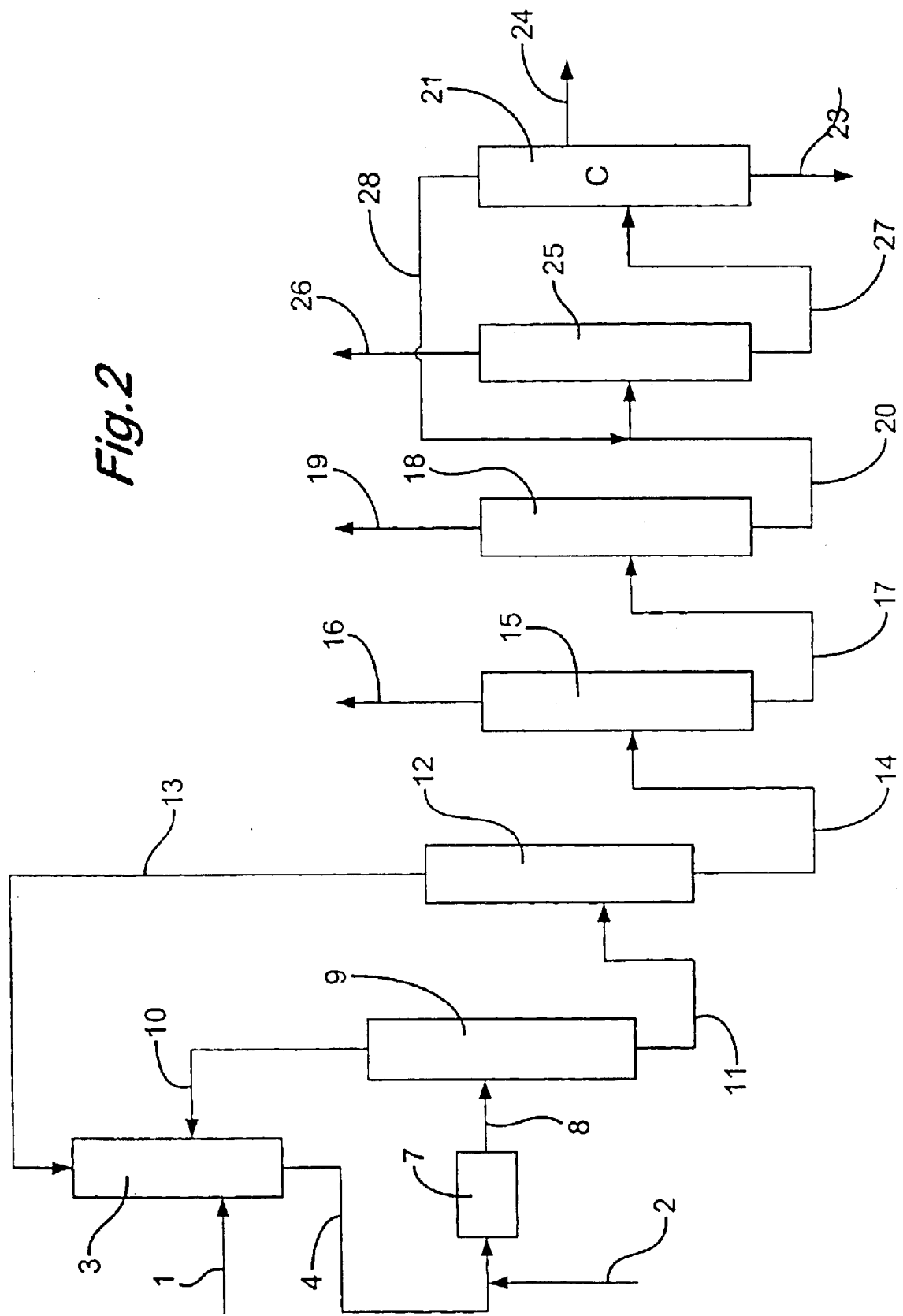
FIG. 2 shows schematically another illustration of the process according to the present invention, in which process a prior distillation makes it possible to separate and isolate a TEA having a degree of purity less than 99%, before the desired TEA is separated and isolated.

In FIGS. 1 and 2, a single distillation column may in fact represent several distillation columns in series.

It is quite surprising to note that the problems of coloration and of instability, especially thermal instability, of TEA over time are solved so efficiently and uniquely by one particular method of separating and isolating the TEA. It is also very surprising that the process according to the present invention allows TEA to be manufactured with a very high purity level and especially with such low secondary dialkanolamine, for example DEA, concentrations despite substantial amounts of secondary dialkanolamine such as DEA, which are present in the specific mixture of alkanolamines subjected to the continuous distillation in order to separate and isolate the desired TEA.

The process comprises a step (i) of synthesizing the TEA by bringing ammonia into contact with ethylene oxide at a temperature that can range from 0 to 150° C., preferably from 20 to 100° C. and especially from 40 to 80° C., and at an absolute pressure that can range from 0.1 to 16 MPa, particularly from 0.2 to 5 MPa, and especially from 0.2 to 2 MPa. The synthesis step may take place in aqueous medium. In that case, the ammonia can be premixed with water, for example in a premixer, so as to form aqueous ammonia which itself will then be brought into contact with ethylene oxide. The reactor used for the synthesis step is preferably a tube reactor.

The products manufactured during the synthesis step may generally comprise a mixture of TEA, DEA, MEA and possibly other heavier ethanolamines such as ethoxylated ethanolamines, in particularly ethoxylated triethanolamines (ETEA), for example the monoglycol ether of triethanolamine. Other products may result from side reactions, in particular glycols such as monoethylene glycol, and aldehydes such as acetaldehyde or formaldehyde. The reaction mixture thus formed during the synthesis step may comprise the abovementioned products, water and unconsumed reactants such as ammonia. The concentration of the abovementioned products and especially of ethanolamines in the reaction mixture depends, among other things, on the relative proportions of ammonia and of ethylene oxide involved in the reaction. The molar ratio of ammonia to ethylene oxide may be between 0.5 and 40, preferably between 1 and 10 and especially between 1.5 and 6. When the synthesis step takes place in aqueous medium, the weight concentration of ammonia in the water may range from 50 to 100%. The reaction mixture obtained during the synthesis step may comprise between 10 and 90%, preferably between 20 and 70% and especially between 30 and 50% by weight of TEA and between 5 and 80%, preferably between 10 and 70%, and especially between 15 and 60% by weight of DEA.

The ethanolamines manufactured during the synthesis step are known by various names. Monoethanolamine (MEA) is also known by the name 2-aminoethanol. Diethanolamine (DEA) is also known by the name 2,2'-iminodiethanol. Triethanolamine (TEA) is also known by the name 2,2'2"-nitrilotriethanol. The ethoxylated triethanolamines (ETEA) are also known by the name glycol ethers of triethanolamine.

The process also comprises a step (ii) of separating the ammonia that has not reacted from the reaction mixture formed in the synthesis step. The ammonia may be separated by means of a fractionation by expansion or, preferably, with the aid of at least one distillation column. When the synthesis step is carried out in aqueous medium, the separation of the ammonia may be followed by a separation of the water from the reaction mixture with the aid of at least one distillation column, or by any means allowing the reaction mixture to be dehydrated.

The ammonia thus separated in step (ii) may advantageously be recycled in the synthesis step, preferably directly in the water/ammonia premixer. If the water is separated, the latter may also be recycled directly into the water/ammonia premixer.

The process also comprises a step (iii) of separating the TEA from the mixture resulting from step (ii), particularly from the mixture of ethanolamines manufactured. The ethanolamines may be separated with the aid of separators such as distillation columns and/or possibly of one or more thin-film evaporators. The MEA and some of the DEA may first of all be separated from the mixture resulting from step (ii) by one or more prior distillations, especially by means of one or more distillation columns, before the desired TEA is separated and isolated.

According to the present invention, TEA may be separated and isolated by a continuous distillation of the specific mixture of alkanolamines comprising TEA and from 0.5 to 50%, preferably 0.5 to 30%, especially 0.5 to 15% and in particular 0.5 to 10% or 0.5 to 5%, for example 1 to 30%, or 1 to 15%, or 1 to 10%, or even 1 to 5%, by weight of at least one secondary dialkanolamine, for example DEA.

According to a preferred method of implementing the present invention, the desired TEA is continuously separated and isolated by lateral withdrawal from a distillation column C continuously fed with the specific mixture of alkanolamines. From the top of the distillation column C, a lighter mixture of alkanolamines comprising the secondary dialkanolamine, e.g. DEA, is preferably withdrawn continuously. The distillation may in particular be carried out in the distillation column C under a vacuum ranging from 68 to 680 Pa (i.e. from 0.5 to 5 mmHg), or from 68 to 407 Pa (i.e. from 0.5 to 3 mmHg), and preferably from 136 to 407 Pa (i.e. from 1 to 3 mmHg), or from 136 to 272 Pa (i.e. from 1 to 2 mmHg), the temperature at the bottom of the column ranging from 155 to 210° C., particularly from 155 to 190° C. and preferably from 165 to 190° C. The total number of theoretical trays may range from 5 to 15, preferably from 7 to 15, knowing that the desired TEA according to the invention may be withdrawn laterally at the height of a theoretical tray lying between the 5th and 10th theoretical trays from the bottom, leaving for example 2 to 5, especially 2 to 4, or 2 to 3 theoretical trays above the point of lateral withdrawal of the desired TEA in order to be able, for example, to withdraw from the top the lightest products such as the secondary dialkanolamines, for example DEA, and also knowing that the specific mixture of alkanolamines according to the invention is fed at a height lying between 3 and 7, preferably between 4 and 5, theoretical trays below the point of lateral withdrawal of the desired TEA and at a height of 3 to 7 theoretical trays from the bottom. The inside of the distillation column is preferably made of stainless steel, for example of the "316 L" type. If the TEA is separated by several distillation columns, it is preferable for the column C to be located in the last position of the said columns. The mixture withdrawn from the top of the column C may essentially comprise from 50 to less than 99%, preferably from 70 to less than 98% and especially from 80 to less than 97% by weight of TEA and from more than 1 to 50%, preferably from more than 2 to 30% and especially from more than 3 to 20% by weight of secondary dialkanolamine, e.g. of DEA. The mixture withdrawn from the bottom of the column C may essentially comprise TEA and ETEAs. The specific mixture of alkanolamines feeding the column C may come from the withdrawal from the bottom of a prior distillation column intended for separating and isolating beforehand some of the DEA existing in the mixture resulting from step (ii).

According to one particular method of implementing the present invention, the specific mixture of alkanolamines feeding the column C may come from the withdrawal from the bottom of a prior distillation column, intended for separating and isolating a TEA having a degree of purity of less than 99% by weight, for example a degree of purity of about 85% by weight, in particular a TEA known commercially as "TEA 85". According to another method of implementation, the mixture withdrawn from the top of the column C may be recycled in a prior distillation column, intended for separating and isolating the DEA, or a TEA having a degree of purity of less than 99% by weight, such as "TEA 85".

The present invention also relates to the TEA that can be preferably obtained by the process according to the present invention and characterized in that the said TEA has:
i) a degree of purity equal to or greater than 99.2%;
ii) a residual content of secondary dialkanolamine, especially DEA, of less than 2000 parts per million by weight (ppm);
iii) a sulphuric ash content of less than 300 ppm, measured according to the V.3.2.14 Standard of the European Pharmacopoeia (1994 Edition); and
iv) a colour index of less than 120 Hazens, measured according to the ASTM D 1209 Standard, after the said TEA has undergone a hot-ageing test at 140° C. in an inert atmosphere for a period of 4 hours.

The TEA preferably is obtainable by the process according to the present invention.

The TEA that can be obtained by the process according to the present invention, after a hot-ageing test at 140° C. in an inert atmosphere, for a period of 4 hours, as described above, has a colour index of less than 120, preferably less than 80, especially less than 40 and more particularly less than 30 or even less than 20 Hazens, the colour index being measured according to the ASTM D1209 Standard.

The TEA that can be obtained by the process according to the present invention, has a degree of purity equal to or greater than 99.2%, preferably equal to or greater than 99.5%, in particular equal to or greater than 99.7% and especially equal to or greater than 99.9% by weight, the degree of purity being measured by gas chromatography analysis.

The TEA that can be obtained by the process according to the present invention, has a residual content of secondary dialkanolamine, particularly DEA, of less than 2000 ppm, preferably less than 1000 ppm and especially less than 500 ppm, for example less than 200 ppm or even less than 100 ppm.

The TEA that can be obtained by the process according to the present invention, may preferably have a residual content of monoethanolamine (MEA) of less than 500 ppm, preferably less than 200 ppm, particularly less than 100 ppm or even less than 50 ppm.

The TEA that can be obtained by the process according to the present invention, has a sulphuric ash content of less than 300 ppm, preferably less than 100 ppm, especially less than 50 and particularly less than 10 ppm or even less than 1 ppm, the sulphuric ash content being measured according to the V.3.2.14 Standard of the European Pharmacopoeia (1994 Edition).

The TEA that can be obtained by the process according to the present invention, may preferably have a colour index of less than 40, preferably less than 20 and especially less than 10 Hazens, the colour index being measured according to the ASTM D1209 Standard on the TEA obtained, for example, just after manufacture or even after storage, but before the hot-ageing test such as that described above.

Advantageously, the TEA that can be obtained by the process according to the present invention, is preferably free of any phosphorus-based and/or possibly boron-based compound. Preferably, the TEA is free of any alkylene oxide, such as ethylene oxide or propylene oxide.

The TEA that can be obtained by the process according to the present invention may especially be an essentially TEA-based mixture:

(a) comprising from 99.2 to 99.9, preferably from 99.5 to 99.9 and particularly from 99.7 to 99.9% by weight of TEA and from 2000 to 50, preferably from 1000 to 50, particularly from 500 to 50 and especially from 200 to 50 ppm of a secondary dialkanolamine, for example DEA, and optionally from 500 to 10, preferably from 200 to 10 and particularly from 100 to 10 ppm of monoethanolamine (MEA); and (b) having a sulphuric ash content of less than 300, preferably less than 100, especially less than 50 and particularly less than 10 or even less than 1 ppm, and a colour index ranging from 120 to 0, preferably from 80 to 0 and particularly from 40 to 0 or from 30 to 0 Hazens after the said TEA has undergone the hot-ageing test at 140° C. in an inert atmosphere for a period of 4 hours.

The degree of purity and the concentration of the products in the desired TEA and in the mixtures, especially for feeding or for withdrawing from the distillation columns, particularly the column C, are measured by gas chromatography analysis. Because of the low elution and the high polarity of the ethanolamines, it is preferable, before the chromatography analysis, to convert the ethanolamines beforehand into fluorinated compounds by a fluorination reaction using, for example, trifluoroacetic anhydride. The fluorination reaction is carried out by bringing 50 mg of an ethanolamine sample into contact with 1 ml of trifluoroacetic anhydride at 15° C. for 10 minutes. The fluorinated products resulting from the reaction are diluted in 1.5 ml of a 4:1 mixture by volume of n-hexane and ethyl acetate and are then analysed by gas chromatography in a 30-meter column of a methylsilicone type with a flame ionization detector.

The method for measuring the colour index of the TEA is that described in the ASTM D1209 Standard. The measurement unit is expressed as the "Hazen", "APHA" or "platinum-cobalt" (or "Pt—Co") colour.

The instability of TEA over time is determined by a hot-ageing test consisting in isolating a 100 g sample of TEA in a closed glass container under an atmosphere of nitrogen and then in placing the container in an oven at 140° C. for 4 hours. After this time, the container is removed from the oven and cooled to the ambient temperature (20° C.), the colour index of the specimen then being measured according to the method described above.

The method for measuring the sulphuric ash contents of the TEA is that described under the reference V.3.2.14 in the European Pharmacopoeia, 1994 Edition.

The examples below show by way of illustration the influence of the selection of secondary dialkanolamines present in the specific mixture of alkanolamines subjected to the continuous distillation for separating and isolating the desired TEA. This influence has an effect on the reduction in the coloration and the thermal stability of the TEA over time.

EXAMPLE 1

Samples consisting of "TEA 99" sold by BP Chemicals as a mixture with DEA were subjected to the hot-ageing test described above. The colour index was measured according to the ASTM D1209 Standard on each specimen before and after the ageing test. The results are given in Table 1.

TABLE 1

| DEA added to the "TEA | Colour index (Hazens) | |
|---|---|---|
| 99" (% by weight) | before the hot-ageing test | after the hot-ageing test |
| 0 | 30 | 150 |
| 1 | 30 | 75 |
| 5 | 30 | 40 |
| 10 | 30 | 30 |

The results in Table 1 show that the presence of DEA in the TEA has an influence on the coloration of the TEA and in particular reduces, or even prevents, the coloration of the TEA after the hot-ageing test. These trials are merely an illustration of the importance of DEA present in the specific mixture of alkanolamines subjected to the distillation which will allow the desired TEA according to the present invention to be separated and isolated.

EXAMPLE 2

Trials identical to those in Example 1 were carried out, except for the fact that, instead of DEA, various organic compounds, added to the TEA in an amount of 5% by weight, were used. Their influence on the coloration and the change in the latter during the hot-ageing test described above were examined.

The various organic compounds used form part of various families of products and are the following:

among primary amines: monohexylamine and monoethanolamine (MEA) (i.e. a primary monoalkanolamine);

among secondary amines: di-n-butylamine, benzylethanolamine (i.e. a secondary monoalkanolamine), diethanolamine (DEA) (i.e. a secondary dialkanolamine) and diisopropanolamine (i.e. a secondary dialkanolamine);

among tertiary amines: tri-n-butylamine, diethylethanolamine (i.e. a tertiary monoalkanolamine) and methyldiethanolamine (i.e. a tertiary dialkanolamine);

among polyols: ethylene glycol and a polyethylene glycol (Mw=200).

Among all these organic compounds added to the TEA subjected to the hot-ageing test, only the products belonging to the family of secondary dialkanolamines (i.e. diethanolamine (DEA) and diisopropanolamine) were able to reduce and even prevent the coloration of the TEA. All the other compounds did not stop the coloration of the TEA.

This series of trials shows that only the secondary dialkanolamines have a favourable influence on the thermal stability of TEA and prevent or substantially reduce the coloration of high-purity TEA.

FIG. 1 shows schematically an illustration of the process according to the present invention.

In FIG. 1, ammonia and ethylene oxide are continuously introduced into a reactor (7) via feed lines (1) and (2) respectively. The ammonia is premixed with water in a premixer (3) to form aqueous ammonia which is withdrawn via a discharge line (4) and then mixed with ethylene oxide via the line (2). The mixture thus produced is introduced into the reactor (7), forming a reaction mixture in which MEA, DEA, TEA and other ethanolamines, such as ETEAs, are formed.

The reaction mixture comprising especially TEA is withdrawn from the reactor (7) via a discharge line (8) and is transferred into a first distillation column (9) used to separate the ammonia which leaves from the top of the column (9). The ammonia is recycled via a line (10) in the premixer (3). A mixture essentially free of ammonia is withdrawn from the bottom of the column (9) and is transferred via a line (11) into a second distillation column (12) used for separating the water. The latter leaves from the top of the column (12) and is recycled in the premixer (3) via a line (13). A mixture essentially comprising ethanolamines free of ammonia and of water is withdrawn from the bottom of the column (12) via a discharge line (14).

The latter mixture is then introduced via the line (14) into a distillation column (15) used for separating and isolating the MEA. At the top of the. column (15), the MEA is extracted via a discharge line (16). A mixture of ethanolamines essentially free of MEA is withdrawn from the bottom of the column (15) and is transferred into a distillation column (18) via a line (17). The column (18) is used to separate and isolate a substantial part of the DEA at the top of the column via a line (19). A mixture of ethanolamines is withdrawn from the bottom of the column (18) via a discharge line (20).

The latter mixture, which corresponds to the specific mixture of alkanolamines essentially comprising TEA and DEA in the amount required according to the present invention, is transferred via the discharge line (20) into a distillation column C (21) intended for separating and isolating the desired high-purity TEA. A lighter mixture containing DEA is withdrawn from the top of the column C (21) via a discharge line (22). A withdrawal from the bottom of the column C (21) makes it possible to extract especially heavy compounds, essentially comprising ETEAs, via a discharge line (23). The desired TEA, which is of high purity, colourless and stable over time, is withdrawn laterally from the column C (21) via a discharge line (24).

FIG. 2 shows schematically another illustration of the process according to the present invention, in which a prior distillation is used for separating and isolating a TEA having a degree of purity of less than 99%, especially equal to 85%.

According to FIG. 2, the process is identical to that described in FIG. 1 except that the mixture flowing in the discharge line (20), essentially comprising TEA and DEA, is transferred via the line (20) into a distillation column (25) intended for separating and isolating a TEA having a degree of purity of less than 99% (for example equal to 85%) at the top of the said column, via a discharge line (26). A mixture which corresponds to the specific mixture of alkanolamines essentially comprising TEA and DEA in the amount required according to the present invention, is withdrawn from the bottom of the column (25) via a line (27) and feeds the column C (21). The mixture withdrawn via the line (28) from the top of the column C (21) is advantageously recycled in the column (25) via the line (20).

What is claim is:

1. A triethanolamine-based mixture having high thermal stability over time for avoiding or reducing coloration thereof comprising from 99.2 to 99.9% by weight of triethanolamine, from 2000 to 50 ppm of a secondary dialkanolamine and optionally from 500 to 10 ppm of monoethanolamine, said triethanolamine-based mixture having:
   i) a sulphuric ash content of less than 300 ppm, measured according to the V.3.2.14 Standard of the European Pharmacopoeia (1994 Edition); and
   ii) a colour index of from 0 to 120 Hazens, measured according to the ASTM D 1209 Standard, after the said triethanolamine-based mixture has undergone a hot-ageing test at 140° C. in an inert atmosphere for a period of 4 hours.

2. The triethanolamine-based mixture of claim 1 comprising from 99.5 to 99.9% by weight of triethanolamine, from 1000 to 50 ppm of a secondary dialkanolamine and optionally from 200 to 10 ppm of monoethanolamine, said triethanolamine-based mixture having:
   i) a sulphuric ash content of less than 100 ppm, measured according to the V.3.2.14 Standard of the European Pharmacopoeia (1994 Edition); and
   ii) a colour index of from 0 to 80 Hazens, measured according to the ASTM D 1209 Standard, after the said triethanolamine-based mixture has undergone a hot-ageing test at 140° C. in an inert atmosphere for a period of 4 hours.

3. The triethanolamine-based mixture of claim 1 comprising from 99.7 to 99.9% by weight of triethanolamine, from 500 to 50 ppm of a secondary dialkanolamine and optionally from 100 to 10 ppm of monoethanolamine, said triethanolamine-based mixture having:
   i) a sulphuric ash content of less than 10 ppm, measured according to the V.3.2.14 Standard of the European Pharmacopoeia (1994 Edition); and
   ii) a colour index of from 0 to 40 Hazens, measured according to the ASTM D 1209 Standard, after the said triethanolamine-based mixture has undergone a hot-ageing test at 140° C. in an inert atmosphere for a period of 4 hours.

4. The triethanolamine-based mixture of claim 1, wherein the secondary dialkanolamine is selected from the group consisting of diethanolamine, diisopropanolamine, di-n-propanolamine and di-n-butanolamine.

5. The triethanolamine-based mixture of claim 1, wherein the secondary dialkanolamine is diethanolamine.

* * * * *